US012144922B2

(12) United States Patent
Carroll et al.

(10) Patent No.: US 12,144,922 B2
(45) Date of Patent: Nov. 19, 2024

(54) WOUND DRESSING WITH MULTIPLE TREATMENT ZONES

(71) Applicant: Solventum Intellectual Properties Company, Maplewood, MN (US)

(72) Inventors: Christopher A. Carroll, San Antonio, TX (US); Christopher Brian Locke, Bournemouth (GB); Shannon C. Ingram, Bulverde, TX (US); Justin Rice, Denver, CO (US)

(73) Assignee: Solventum Intellectual Properties Company, Maplewood, MN (US)

( * ) Notice: Subject to any disclaimer, the term of this patent is extended or adjusted under 35 U.S.C. 154(b) by 43 days.

(21) Appl. No.: 17/624,958

(22) PCT Filed: Jul. 16, 2020

(86) PCT No.: PCT/IB2020/056709
§ 371 (c)(1),
(2) Date: Jan. 5, 2022

(87) PCT Pub. No.: WO2021/009712
PCT Pub. Date: Jan. 21, 2021

(65) Prior Publication Data
US 2022/0288297 A1    Sep. 15, 2022

Related U.S. Application Data

(60) Provisional application No. 62/875,352, filed on Jul. 17, 2019.

(51) Int. Cl.
*A61M 1/00*  (2006.01)
*A61F 13/05* (2024.01)

(52) U.S. Cl.
CPC ............. *A61M 1/912* (2021.05); *A61F 13/05* (2024.01)

(58) Field of Classification Search
CPC ........ A61M 1/92; A61M 1/912; A61M 1/913; A61M 1/915; A61M 1/918; A61M 13/022;
(Continued)

(56) References Cited

U.S. PATENT DOCUMENTS 1,355,846 A   10/1920  Rannells
2,547,758 A    4/1951  Keeling
(Continued)

FOREIGN PATENT DOCUMENTS

AU   550575 B2   3/1986
AU   745271 B2   3/2002
(Continued)

OTHER PUBLICATIONS

International Search Report and Written Opinion for Corresponding Application No. PCT/IB2020/056709, mailed Sep. 9, 2020.
(Continued)

*Primary Examiner* — Leslie A Lopez
*Assistant Examiner* — Timothy L Flynn

(57) ABSTRACT

A customizable wound treatment system for treating multiple zones of a wound includes a dressing configured for use with a first zone and a second zone of a wound that includes a first foam layer placed over the first zone, a second foam layer placed over the second zone, a first drape layer disposed over the first foam layer and beneath the second foam layer, and a second drape layer disposed over the second foam layer. The customizable wound treatment system includes a negative pressure source pneumatically coupled to the first foam layer and the second foam layer and operable to create a negative pressure at the first zone and the second zone and a fluid instillation pump fluidly coupled to the first foam layer and configured to instill a treatment fluid to the first zone.

11 Claims, 11 Drawing Sheets

(58) Field of Classification Search
CPC ........ A61M 13/00068; A61M 13/0216; A61M 1/90; A61M 1/91; A61M 1/917; A61M 27/00; A61F 13/00068; A61F 13/022; A61F 13/0216; A61F 13/05; A61F 13/0203; A61F 2013/0054
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2003/0050594 A1* | 3/2003 | Zamierowski ........ A61M 27/00 604/24 |
| 2009/0227969 A1 | 9/2009 | Jaeb et al. |
| 2011/0257573 A1 | 10/2011 | Hong et al. |
| 2014/0163491 A1 | 6/2014 | Schuessler et al. |
| 2015/0080788 A1 | 3/2015 | Blott et al. |
| 2017/0182230 A1* | 6/2017 | Ingram ............... A21B 3/18 |
| 2018/0214315 A1 | 8/2018 | Mercer et al. |
| 2018/0243463 A1* | 8/2018 | Chatterjee ........... A61L 15/58 |
| 2019/0099293 A1* | 4/2019 | Hall .................. A61F 13/05 |
| 2019/0231944 A1* | 8/2019 | Dunn ................ A61M 1/916 |
| 2020/0069850 A1* | 3/2020 | Beadle ............... A61M 1/985 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |

(56) References Cited

FOREIGN PATENT DOCUMENTS

| GB | 2195255 A | 4/1988 |
|---|---|---|
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al.; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sept. 3, 1997.
Dattilo, Philip P., Jr., et al.; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al.; "Vacuum Treatment in the Surgical Management of Purulent Wounds"; Vestnik Khirurgi, Sep. 1986, pp. 18-21 and 6 page English translation thereof.
Davydov, Yu. A., et al.; "Vacuum Therapy in the Treatment of Purulent Lactation Mastitis"; Vestnik Khirurgi, May 14, 1986, pp. 66-70, and 9 page English translation thereof.
Yusupov. Yu.N., et al.; "Active Wound Drainage", Vestnki Khirurgi, vol. 138, Issue 4, 1987, and 7 page English translation thereof.
Davydov, Yu.A., et al.; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al.; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al.; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Bjorn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

(56) References Cited

OTHER PUBLICATIONS

V.A.C. @ Therapy Clinical Guidelines: A Reference Source for Clinicians; Jul. 2007.

* cited by examiner

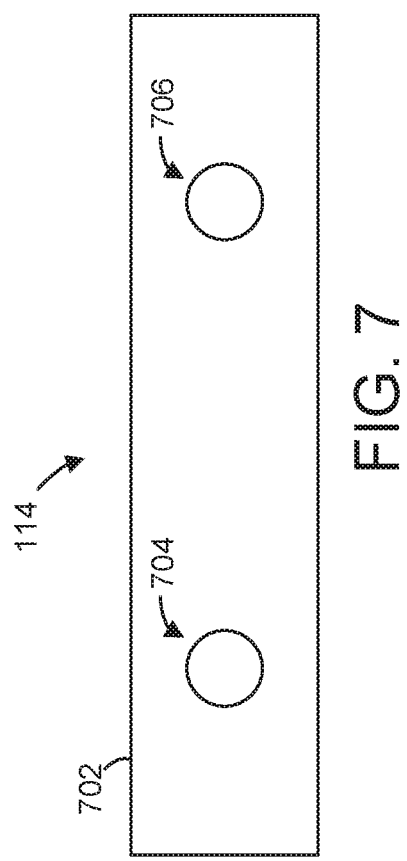

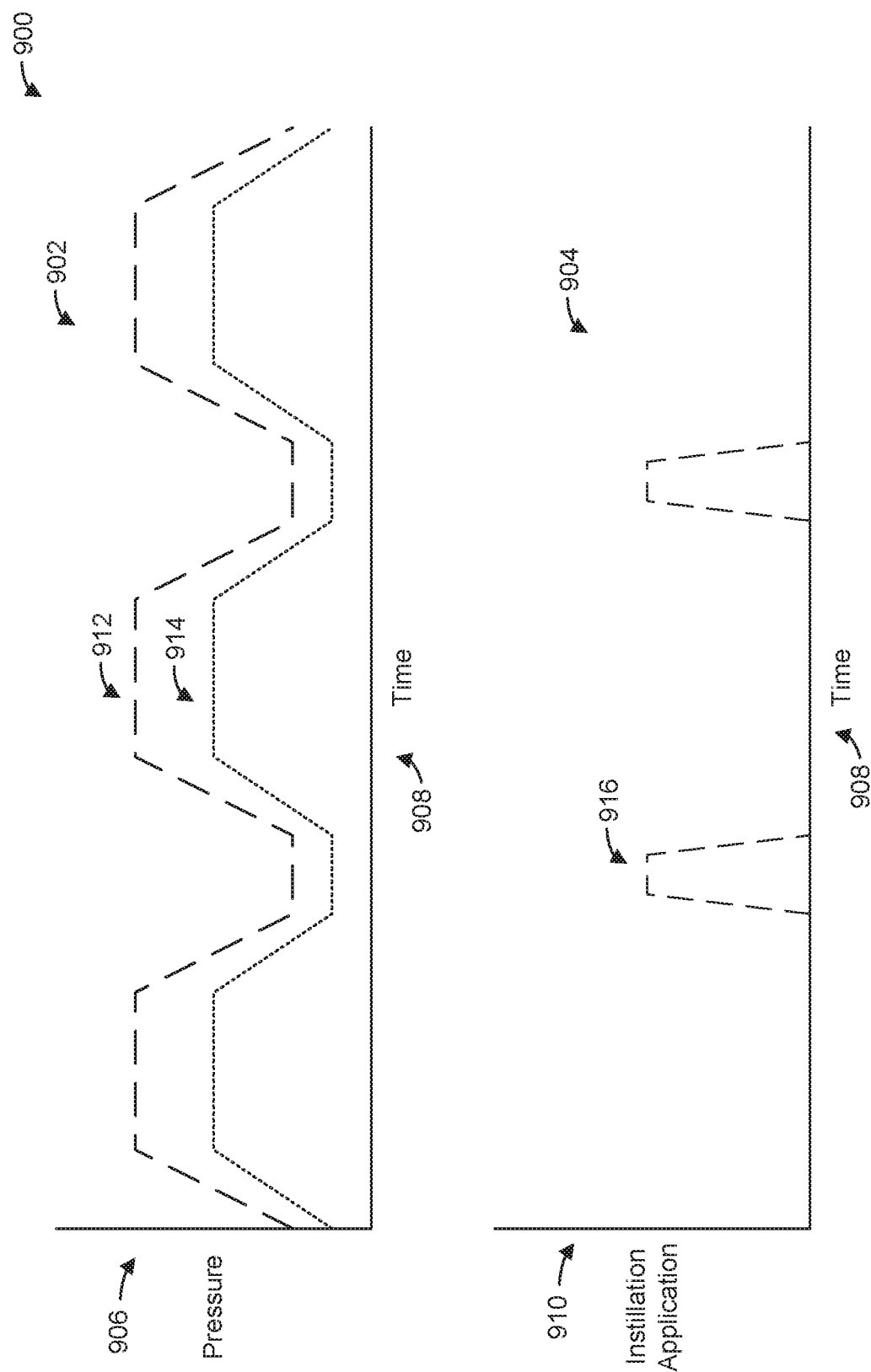

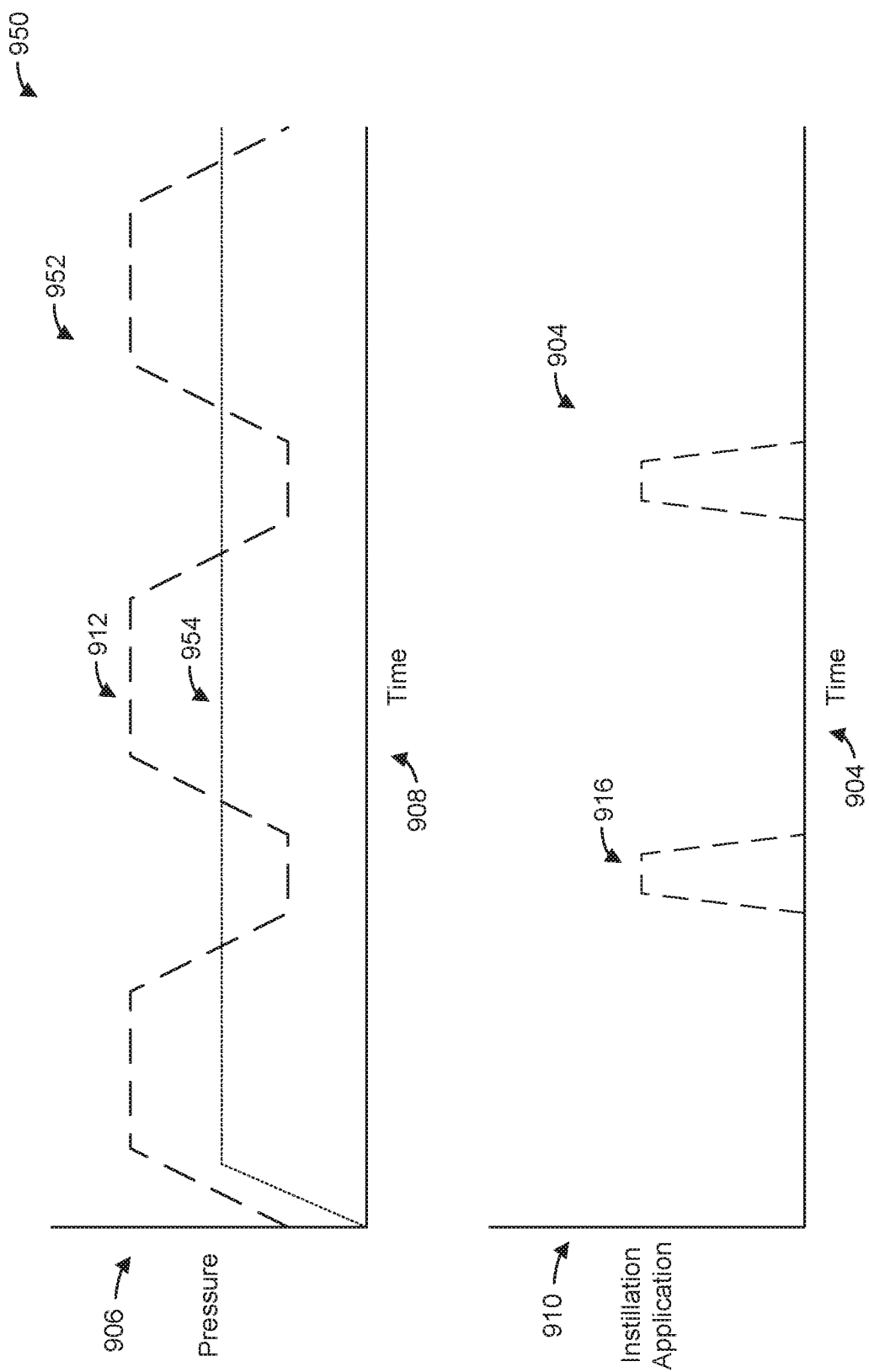

WOUND DRESSING WITH MULTIPLE TREATMENT ZONES

CROSS-REFERENCE TO RELATED APPLICATIONS

This application claims the benefit of priority to U.S. Provisional Application No. 62/875,352, filed on Jul. 17, 2019, which is incorporated herein by reference in its entirety.

BACKGROUND

The present disclosure relates generally to the field of treating wounds. The present disclosure relates more specifically to dressings capable of applying different wound treatment therapies to different zones of a wound.

Existing dressings for applying wound treatment therapies pose numerous disadvantages, including: inability to apply different instillation therapies to different wound zones; inability to apply different negative pressure cycles across different wound zones; inability to fluidly isolate different wound zones; etc. Given the limitations of existing dressings for applying wound treatment therapies, it may be desirable to provide a means of isolation between the different zones of a wound such that different wound treatment therapies may be applied to the different zones of the wound.

SUMMARY

One implementation of the present disclosure is a customizable wound treatment system for treating multiple zones of a wound. The customizable wound treatment system includes a dressing configured for use with a first zone and a second zone of the wound that includes a first foam layer configured for placement over the first zone, a second foam layer configured for placement over the second zone, a first drape layer disposed over the first foam layer and beneath the second foam layer, and a second drape layer disposed over the second foam layer. The customizable wound treatment system also includes a negative pressure source pneumatically coupled to the first foam layer and the second foam layer and operable to create a negative pressure at the first zone and the second zone and a fluid instillation pump fluidly coupled to the first foam layer and configured to instill a treatment fluid to the first zone. The first zone can include a wound bed of the wound and the second zone can include a periwound of the wound.

In some embodiments, the first drape layer and the second drape layer pneumatically and fluidly isolate the first foam layer and the second foam layer from each other.

In some embodiments, the negative pressure source is operable to provide a common negative pressure regimen to both the first zone and the second zone. The negative pressure source is also operable to simultaneously provide a first negative pressure regimen to the first zone and a second negative pressure regimen to the second zone such that the first negative pressure regimen is different from the second negative pressure regimen.

In some embodiments, the first foam layer is disposed above the first zone and the second foam layer is disposed above the second zone in a concentric pattern. The second foam layer may extend beyond a perimeter of the first foam layer.

In some embodiments, the first foam layer is formed of a first foam material and the second foam layer is formed of a second foam material. The first foam material may comprise a first density and the second foam material may comprise a second density that is greater than the first density.

In some embodiments, the second foam layer comprises holes extending therethrough.

Another implementation of the present disclosure is a system for use with at least two wound zones to apply at least two different wound therapies. The system includes a first foam layer configured for placement over a first wound zone, a second foam layer configured for placement over a second wound zone, a first drape layer disposed over the first foam layer and beneath the second foam layer and configured to isolate the first wound zone from the second wound zone, a second drape layer disposed over the second foam layer and the first drape layer and configured to isolate the first wound zone and the second wound zone from an external environment, an instillation pump that provides an instillation fluid to the first foam layer, a negative pressure pump configured to remove air from the first wound zone and the second wound zone, and a control circuit communicably coupled to the instillation pump and the negative pressure pump.

In some embodiments, the control circuit controls the instillation pump to provide an amount of instillation fluid to the first foam layer, provide a soak period. The control circuit controls the negative pressure pump to provide at least one cyclic variation of negative pressure at the first wound zone and the second wound zone.

In some embodiments, the system includes a manifold that fluidly communicates the negative pressure pump with the first wound zone and the second wound zone. The manifold is configured to fluidly communicate the first foam layer with the instillation pump via a first tube. The manifold includes a first and second aperture and fluidly communicates the first foam layer and the second foam layer with the negative pressure pump via a first tube and a second tube.

In some embodiments, the manifold includes a single aperture and to fluidly communicate the first foam layer and the second foam layer with the negative pressure pump via a first tube.

In some embodiments, the manifold is configured to isolate a first cyclic variation of negative pressure applied to the first wound zone from a second cyclic variation of negative pressure applied to the second wound zone.

In some embodiments, the manifold fluidly couples the instillation pump with the second foam layer.

In some embodiments, the negative pressure pump applies a first cyclic variation of negative pressure to the first foam layer and a second cyclic variation of negative pressure to the second foam layer.

In some embodiments, the first drape layer includes a first drape aperture configured to receive a first tube and the second drape layer includes a second drape aperture configured to align with the first drape aperture and receive the first tube. The second drape layer can include a third drape aperture configured to receive a second tube. The manifold can include a first aperture and a second aperture configured to align with a second drape aperture and a third drape aperture.

In some embodiments, the control circuit is configured to simultaneously control the negative pressure pump to provide at least one cyclic variation of negative pressure at the first foam layer and the second foam layer and control the instillation pump to provide the instillation fluid to the first foam layer.

In some embodiments, the control circuit is configured to apply a first cyclic variation of negative pressure to the first wound zone and a second cyclic variation of negative pressure to the second wound zone.

In some embodiments, the control circuit is configured to apply a first constant negative pressure to the first wound zone and a second constant negative pressure to the second wound zone.

In some embodiments, the control circuit is configured to control the negative pressure pump to simultaneously provide a constant negative pressure to the first wound zone and a cyclic variation of negative pressure to the second wound zone.

In some embodiments, the different wound therapies include a first wound therapy applied to the first wound zone including a first application of negative pressure and a first application of instillation and a second wound therapy applied to the second wound zone including a second application of negative pressure and a second application of instillation. The different wound therapies can include a user selection of the different wound therapies.

Another implementation of the present disclosure is a method for applying different wound therapies to wound zones. The method includes placing a first foam layer over a first wound zone, placing a second foam layer over a second wound zone, placing a first drape layer over the first foam layer and beneath the second foam layer, covering the second foam layer with a second drape layer, providing a manifold that bridges between and fluidly communicates with the first foam layer and the second foam layer and with an instillation pump and a negative pressure pump, applying a first wound therapy to the first wound zone, and applying a second would therapy to the second wound zone.

In some embodiments, placing the first foam layer over the first wound zone involves fitting the first foam layer to the first wound zone and placing the second foam layer over the second wound zone involves fitting the second foam layer to the second wound zone.

In some embodiments, applying the first wound therapy to the first wound zone involves applying a first application of negative pressure to the first wound zone and applying a first application of instillation to the first wound zone.

In some embodiments, applying the first application of negative pressure to the first wound zone involves applying a first constant negative pressure to the first wound zone.

In some embodiments, applying the first application of negative pressure to the first wound zone involves applying a first cyclic variation of negative pressure to the first wound zone.

In some embodiments, applying a second wound therapy to the second wound zone involves applying a second application of negative pressure to the second wound zone and applying a second application of instillation to the second wound zone. Applying the second application of negative pressure to the second wound zone can involve applying a second constant negative pressure to the second wound zone.

In some embodiments, applying the second application of negative pressure to the second wound zone involves applying a second cyclic variation of negative pressure to the second wound zone.

Yet another implementation of the present disclosure is a wound dressing for simultaneously treating a first wound zone that encases a wound bed and a second wound zone that encases an area surrounding the wound bed. The wound dressing includes a first foam layer configured for placement over the first wound zone, a first film cover disposed over the first foam layer and including a first aperture, a fenestrated film layer disposed over the first film cover and overlapping the second wound zone and including a second aperture, a second foam layer disposed over the fenestrated film layer and including a third aperture, a drape layer disposed over the second foam layer and including a fourth aperture formed therein, and a fitting including a tubular portion and a flange portion. The tubular portion is configured to extend through the first aperture, the second aperture, the third aperture, and the fourth aperture, fluidly communicate with the first foam layer and the fenestrated film layer, and draw a negative pressure through the first foam layer and the second foam layer.

In some embodiments, the fitting pneumatically communicates the first foam layer and the second foam layer with a negative pressure pump. The fitting can pneumatically communicate the first foam layer with an instillation pump.

In some embodiments, the negative pressure pump is operable to provide a common negative pressure to both the first wound zone and the second wound zone. The negative pressure pump can be operable to simultaneously provide a first negative pressure regimen to the first wound zone and a second negative pressure regimen to the second wound zone.

In some embodiments, the first negative pressure regimen is different than the second negative pressure regimen.

Another implementation of the present disclosure is a customizable wound treatment system for treating multiple zones of a wound. The customizable wound treatment system includes a dressing configured for use with a first zone and a second zone of the wound that includes a first foam layer configured for placement over the first zone, a second foam layer configured for placement over the second zone, a first drape layer disposed over the first foam layer, and a second drape layer disposed over the second foam layer. The customizable wound treatment system also includes a negative pressure source pneumatically coupled to the first foam layer and the second foam layer and operable to create a negative pressure at the first zone and the second zone and a fluid instillation pump fluidly coupled to the first foam layer and configured to instill a treatment fluid to the first zone. The first zone can include a wound bed of the wound and the second zone can include a periwound of the wound.

In some embodiments, the first drape layer and the second drape layer pneumatically and fluidly isolate the first foam layer and the second foam layer from each other.

In some embodiments, the negative pressure source is operable to provide a common negative pressure regimen to both the first zone and the second zone. The negative pressure source is also operable to simultaneously provide a first negative pressure regimen to the first zone and a second negative pressure regimen to the second zone such that the first negative pressure regimen is different from the second negative pressure regimen.

In some embodiments, the first foam layer is disposed above the first zone and the second foam layer is disposed above the second zone in a concentric pattern. The second foam layer may extend beyond a perimeter of the first foam layer.

In some embodiments, the first foam layer is formed of a first foam material and the second foam layer is formed of a second foam material. The first foam material may comprise a first density and the second foam material may comprise a second density that is greater than the first density.

In some embodiments, the second foam layer comprises holes extending therethrough.

BRIEF DESCRIPTION OF THE DRAWINGS

Various objects, aspects, features, and advantages of the disclosure will become more apparent and better understood by referring to the detailed description taken in conjunction with the accompanying drawings, in which like reference characters identify corresponding elements throughout. In the drawings, like reference numbers generally indicate identical, functionally similar, and/or structurally similar elements.

FIG. 7 is an illustration of a manifold used with the first wound zone separation system of FIG. 1A, according to an exemplary embodiment.

FIG. 9A is an illustration of a first application of multiple wound treatment therapies, according to an exemplary embodiment.

FIG. 9B is an illustration of a second application of multiple wound treatment therapies, according to an exemplary embodiment.

DETAILED DESCRIPTION

Wound Zone Separation System

Figure 1A:
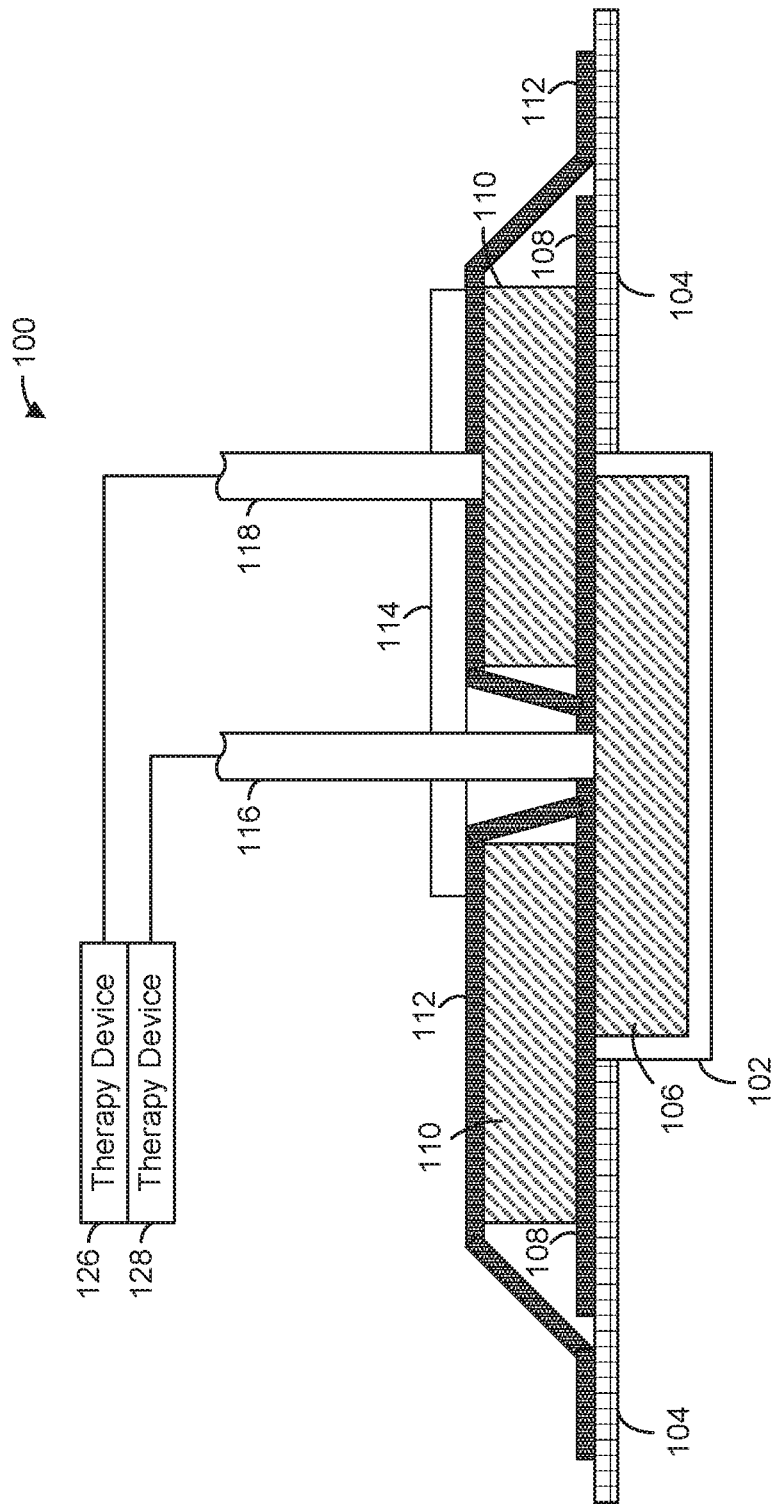
FIG. 1A is a first wound zone separation system, according to an exemplary embodiment.
Figure 2A:
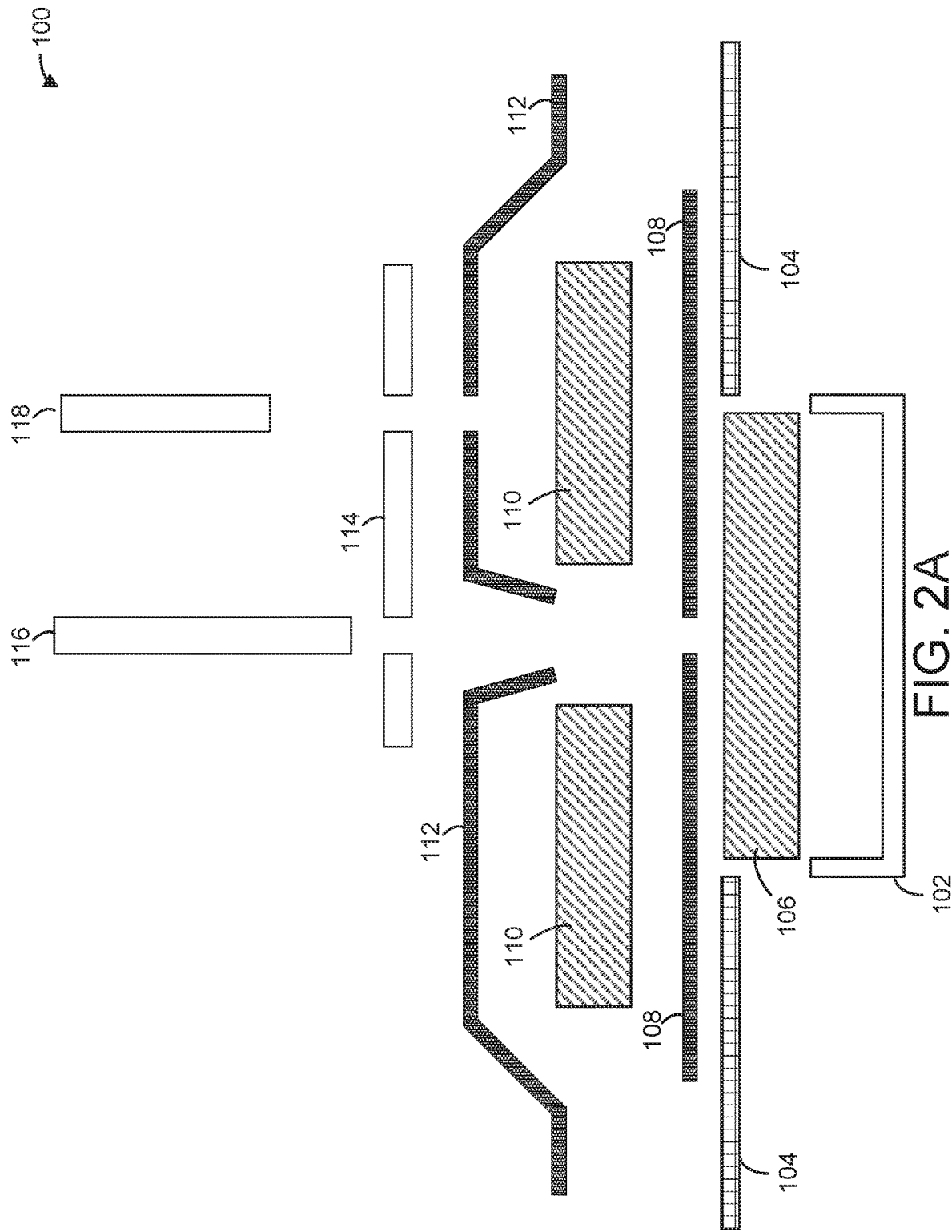
FIG. 2A is an exploded view illustrating the first wound zone separation system of FIG. 1A, according to an exemplary embodiment.

Referring now to FIGS. 1A & 2A, a wound zone separation system 100 is shown, according to a first embodiment. As will be explained in further detail, wound zone separation system 100 may be configured to isolate (e.g., fluidly, physically, etc.) various zones of a wound. Additionally, wound zone separation system 100 may be configured to apply different wound therapy treatments to different wound zones. For example, wound zone separation system 100 may be able to apply a negative differential pressure treatment and/or a fluid instillation treatment to a first wound zone 102 (shown as a wound bed) via a first tube 116 and a second wound zone shown 104 (shown as a periwound) via a second tube 118. The examples described herein are not intended to be limiting. Wound zone separation system 100 may include any additional features, components, or modules to allow for customization of applying multiple wound treatment therapies to multiple wound zones.

Wound zone separation system 100 is shown as a single dressing for use at a wound site having two or more wound zones. As shown in FIGS. 1A & 2A, the dressing is applied to first wound zone 102 and second wound zone 104, according to an exemplary embodiment. First wound zone 102, illustrated as a wound bed in the exemplary embodiment, may be the immediate location of a wound (e.g., sore, laceration, burn, etc.). First tube 116 may be configured to communicate (e.g., fluidly, pneumatically, etc.) with first wound zone 102 and apply a first wound treatment therapy (e.g., instillation therapy, negative pressure therapy, etc.) from a therapy device 126. Second wound zone 104, illustrated as a periwound in the exemplary embodiment, may be the area substantially surrounding the area of first wound zone 102. Second tube 118 may be configured to communicate (e.g., fluidly, pneumatically, etc.) with second wound zone 104 and apply a second wound treatment from a therapy device 128. As will be described, wound zone separation system 100 may include features configured to couple (e.g., fluidly, physically, etc.) and/or isolate (e.g., fluidly, physically, etc.) first wound zone 102 and second wound zone 104 with the components of wound zone separation system 100.

Still referring to FIGS. 1A & 2A, wound zone separation system 100 is shown to include a first foam layer 106 configured for placement over the first wound zone 102. Referring to FIG. 2A, in some embodiments, first foam layer 106 may be customized (e.g., fitted, selected) for placement on or within a volume defined by first wound zone 102. First foam layer 106 may couple (e.g., pneumatically, fluidly, etc.) first tube 116 with first wound zone 102. As will be understood, first foam layer 106 may be formed of a material configured to allow the flow of air, fluid, debris, etc. to flow therethrough, i.e., to flow from first wound zone 102 to first tube 116.

Wound zone separation system 100 is shown to include a first drape layer 108 configured for placement over first foam layer 106 and at least partially over second wound zone 104. Referring to FIG. 2A, first drape layer 108 may be customized (e.g., fitted, selected) for placement over an area larger than an area covered by first foam layer 106. As will be described, first drape layer 108, may be sealable over first wound zone 102 and at least a portion of second wound zone 104 in a substantially airtight manner to allow a pressure differential to be maintained across the first drape layer 108.

Still referring to FIGS. 1A & 2A, wound zone separation system 100 is shown to include a second foam layer 110 which may be configured for placement over second wound zone 104. In some embodiments, second foam layer 110 may also be configured for placement over at least a portion of first wound zone 102. Referring to FIG. 2A, in some embodiments, second foam layer 110 may be customized (e.g., fitted, selected) for placement over an area defined by second wound zone 104 and may provide a central cutout configured for placement around first wound zone 102. According to various embodiments, second foam layer 110 may couple (e.g., pneumatically, fluidly, etc.) second tube 118 with second wound zone 104. As will be understood, second foam layer 110 may be formed of a material configured to allow the flow of air, fluid, debris, etc. to flow therethrough, i.e., to flow from second wound zone 104 to second tube 118.

Wound zone separation system 100 is also shown to include a second drape layer 112 configured for placement over second foam layer 110 and first drape layer 108. Referring to FIG. 2A, second drape layer 112 may be customized (e.g., fitted, selected) for placement over an area larger than an area covered by first drape layer 108. As will be described, second drape layer 112, may be sealable over second wound zone 104 in a substantially airtight manner to allow a pressure differential to be maintained across the second drape layer 112. Additionally, second drape layer 112 may be configured to isolate (e.g., pneumatically, fluidly, physically, etc.) first wound zone 102 and second wound zone 104 from an external environment.

Still referring to FIGS. 1A & 2A, wound zone separation system 100 is shown to include a manifold 114 configured for placement over second drape layer 112. In other embodiments, wound zone separation system 100 may not include manifold 114. As will be understood, in some embodiments, manifold 114 may be customized to couple (e.g., fluidly, pneumatically, etc.) first wound zone 102 with a negative pressure pump and/or an instillation pump via first foam layer 106 and first tube 116. Additionally, in some embodiments, manifold 114 may be customized to couple (e.g., fluidly, pneumatically, etc.) second wound zone 104 with a negative pressure pump and/or an instillation pump via second foam layer 110 and second tube 118.

Wound zone separation system 100 is also shown to include first tube 116 and second tube 118. In some embodiments, wound zone separation system 100 may include any number of tubes. First tube 116 and second tube 118 may be defined according to any number of, and combination of desired dimensions, shapes, sizes, features, configurations, and other characteristics, and may be formed of any number of, or combination of, different materials. First tube 116 and second tube 118 may include any additional features and/or components (e.g., y-connectors, couplers, threaded surfaces, etc.) to facilitate the application of one or more wound treatment therapies. As will be further described, first tube 116 and second tube 118 may be configured to couple the various components of wound zone separation system 100, first wound zone 102, and second wound zone 104 with therapy device 126 and/or therapy device 128.

As illustrated in FIG. 1A, therapy device 126 and therapy device 128 are shown to be provided as individual devices, according to an exemplary embodiment. In some embodiments, therapy device 126 and therapy device 128 may be provided as individual devices operating with a single use. For example, therapy device 126 may operate as a negative pressure pump while therapy device 128 may operate as a fluid instillation pump. In other embodiments, therapy device 126 and therapy device 128 may be included as one unit with multiple uses. For example, therapy device 126 and therapy device 128 may operate as a unitary device providing both a fluid instillation source as well as a negative pressure source. Further, in some embodiments, therapy device 126 and therapy device 128 may each be capable of multiple uses (e.g., a negative pressure pump and a fluid instillation pump) that may or may not be controller independently of the other.

Figure 1B:
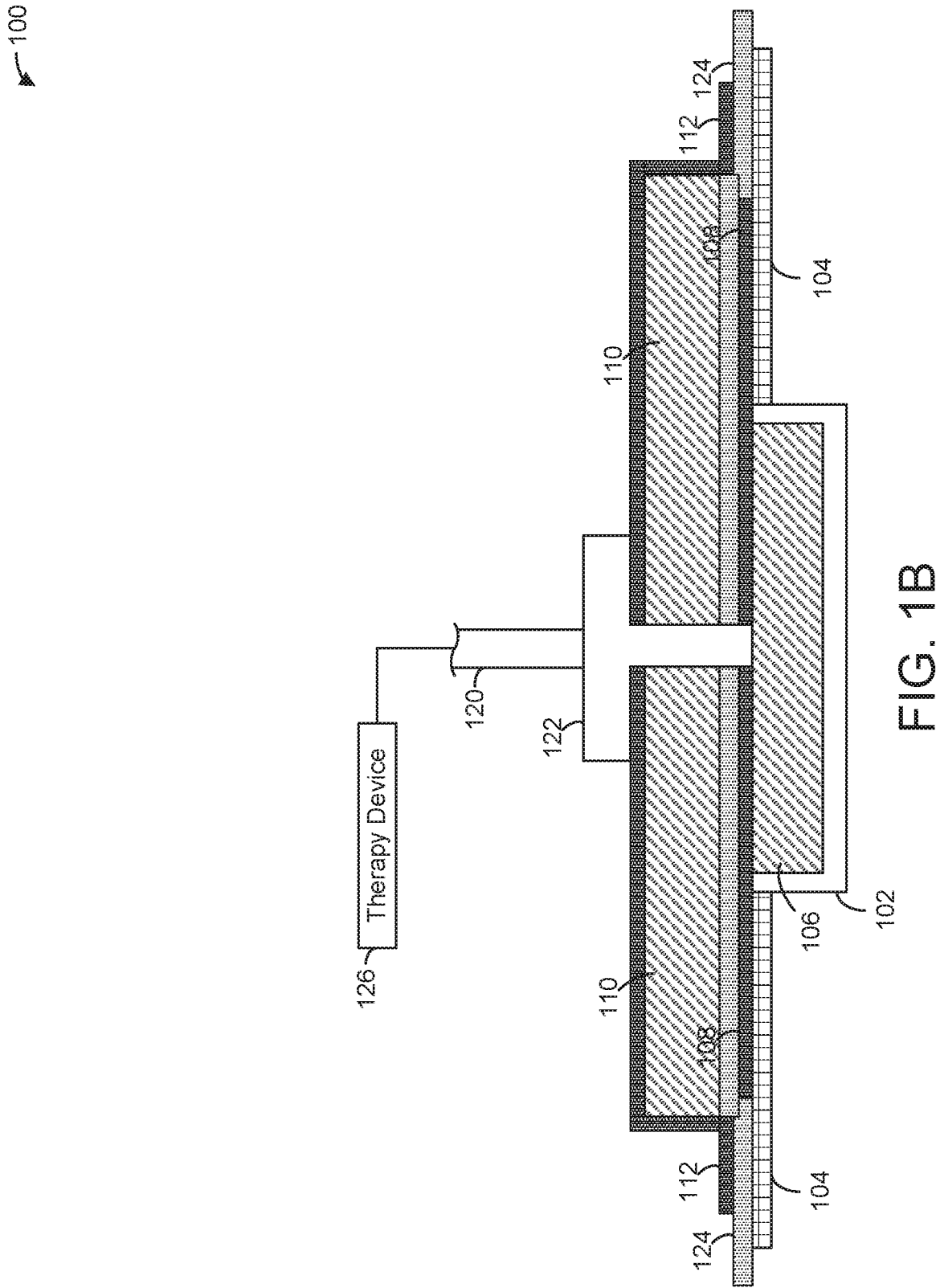
FIG. 1B is a second wound zone separation system, according to an exemplary embodiment.
Figure 2B:
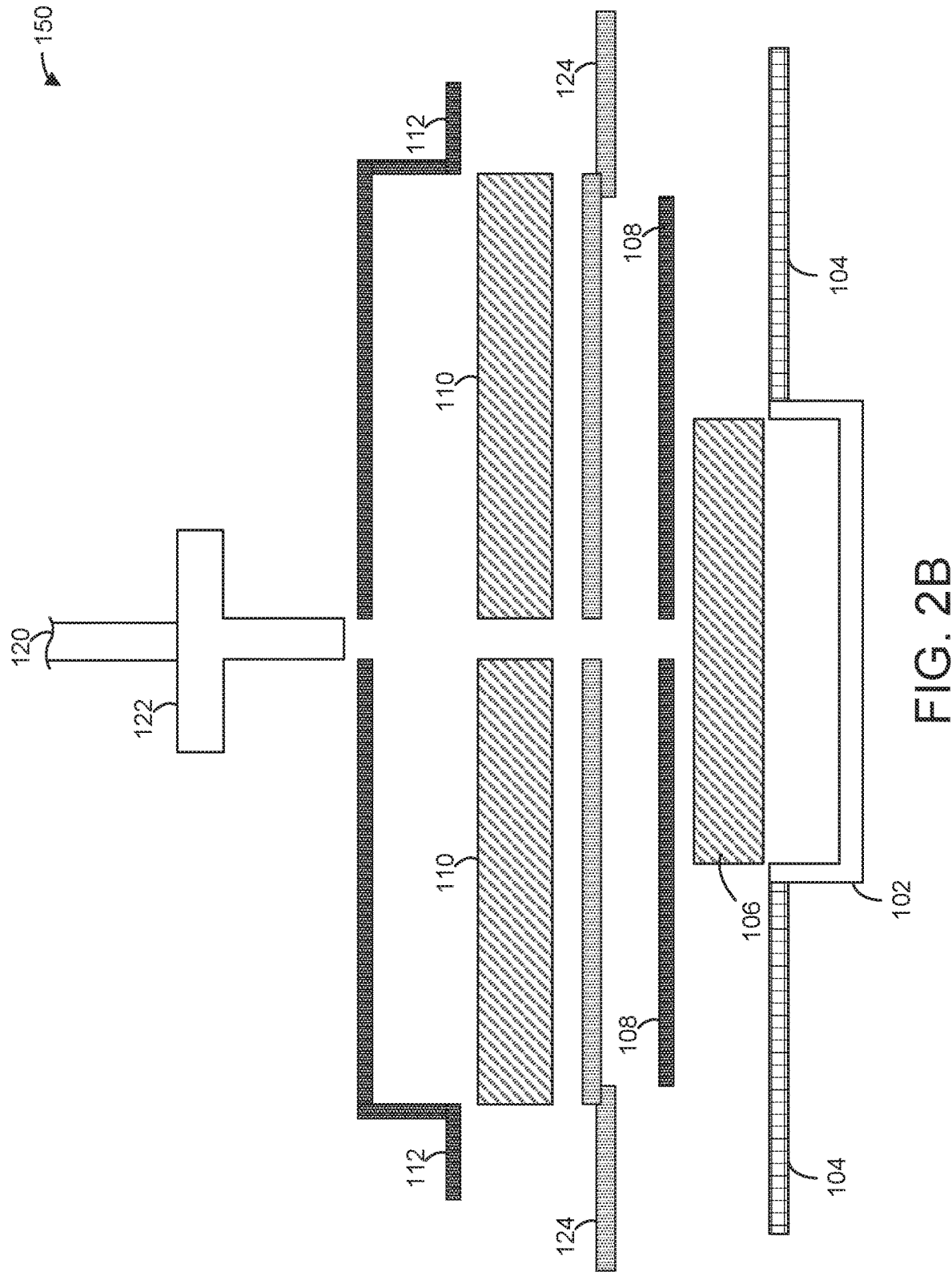
FIG. 2B is an exploded view illustrating the second wound zone separation system of FIG. 1B, according to an exemplary embodiment.

Referring now to FIGS. 1B & 2B, a second embodiment of wound zone separation system 100 is shown, according to an exemplary embodiment. In the second embodiment, wound zone separation system 100 may be configured to isolate (e.g., fluidly, physically, pneumatically, etc.) various zones of a wound. Additionally, wound zone separation system 100 may be configured to apply different wound treatment therapies to various wound zones via a tube 120 and a fitting 122. Referring specifically to FIG. 1B, the second embodiment of wound zone separation system 100 is shown to apply a wound therapy treatment to first wound zone 102 and second wound zone 104 from therapy device 126 via tube 120. The second embodiment of wound zone separation system 100 may include any additional features, components, or modules to allow for customization of applying wound treatment therapies to multiple wound zones.

Similar to the first embodiment of FIGS. 1A & 2A, the second embodiment of wound zone separation system 100 illustrated in FIGS. 1B & 2B is shown to include first foam layer 106 configured for placement over the first wound zone 102. Referring to FIG. 2B, first foam layer 106 may be customized (e.g., fitted, selected) for placement within a volume defined by first wound zone 102. According to various embodiments, first foam layer 106 may couple (e.g., pneumatically, fluidly, etc.) tube 120 with first wound zone 102.

The second embodiment of wound zone separation system 100 is also shown to include first drape layer 108, according to exemplary embodiments. First drape layer 108 may be configured for placement over first foam layer 106 and at least partially over second wound zone 104. Referring to FIG. 2B, in some embodiments, first drape layer 108 may be customized (e.g., fitted, selected) for placement over an area larger than an area covered by first foam layer 106. As will be described, first drape layer 108, may be sealable over first wound zone 102 and at least a portion of second wound zone 104 in a substantially airtight manner to allow a pressure differential to be maintained across the first drape layer 108.

Still referring to FIGS. 1B & 2B, the second embodiment of wound zone separation system 100 is shown to include a fenestrated film layer 124 configured for placement over first drape layer 108 and substantially over second wound zone 104. Referring to FIG. 2B, in some embodiments, fenestrated film layer 124 may be customized (e.g., fitted, selected, etc.) for placement over an area larger than an area covered by first drape layer 108. Fenestrated film layer 124 may be formed of a material configured to allow the flow of air, fluid, debris, etc. to flow therethrough, i.e., to flow from a surface of fenestrated film layer 124 nearest the second wound zone 104 to a surface of fenestrated film layer 12 furthest the second wound zone 104.

The second embodiment of wound zone separation system 100 is shown to include second foam layer 110 configured for placement over fenestrated film layer 124. In some embodiments, second foam layer 110 may be configured for placement over at least a portion of first wound zone 102. Second foam layer 110 may couple (e.g., pneumatically, fluidly, etc.) fitting 122 with fenestrated film layer 124. As will be understood, second foam layer 110 may be formed of a material configured to allow the flow of air, fluid, debris, etc. to flow therethrough, i.e., to flow from fenestrated film layer 124 to fitting 122.

Still referring to FIGS. 1B & 2B, the second embodiment of wound zone separation system 100 is shown to include second drape layer 112 configured for placement over second foam layer 110. Referring to FIG. 2B, in some embodiments, second drape layer 112 may be customized (e.g., fitted, selected) for placement over an area larger than an area covered by second foam layer 110. As will be described, second drape layer 112, may be sealable over second wound zone 104 in a substantially airtight manner to allow a pressure differential to be maintained across the second drape layer 112. Additionally, second drape layer 112 may be configured to isolate the first wound zone 102 and second wound zone 104 from an external environment.

The second embodiment of wound zone separation system 100 is also shown to include a fitting 122 configured to couple the various components of wound zone separation system 100, first wound zone 102, and second wound zone 104 with a tube 120. As will be described, fitting 122 may include features configured to apply different wound treatment therapies to first wound zone 102 and second wound zone 104 via tube 120.

Still referring to FIGS. 1B & 2B, the second embodiment of wound zone separation system 100 is shown to include tube 120. Tube 120 may be defined according to any number of, and combination of desired dimensions, shapes, sizes, features, configurations, and other characteristics, and may be formed of any number of, or combination of, different materials. As will be further described, tube 120 may be configured to couple the various components of wound zone separation system 100, first wound zone 102, and second wound zone 104 with therapy device 126. Further, as will be described, tube 120 may be configured to simultaneously apply a negative pressure therapy along with an instillation therapy administered by therapy device 126.

First Foam Layer

Figure 3:
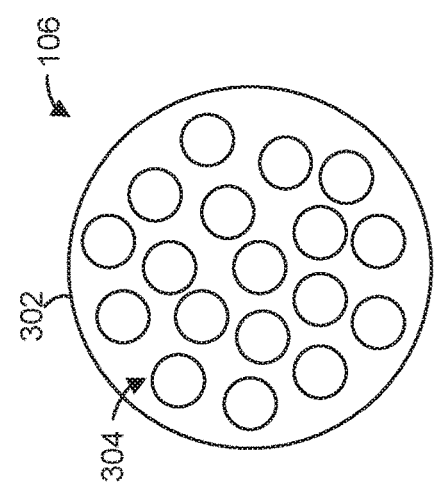
FIG. 3 is an illustration of a first foam layer used with the first wound zone separation system of FIG. 1A, according to an exemplary embodiment.

Referring now to FIG. 3, a top view of first foam layer 106 is shown, according to an exemplary embodiment. First foam layer 106 may be defined according to any number of, and combination of, desired dimensions, shapes, sizes, features, configurations, and other characteristics, and may be formed of any number of, or combination of, different materials. In the exemplary embodiment of FIG. 3, first foam layer 106 is defined by a first foam material 302 (e.g., GRANUFOAM™ Dressing, V.A.C. VERAFLO CLEANSE CHOICE™ Dressing/Dressing Kit, etc.) having a first density and providing multiple holes 304 extending therethrough. In various embodiments, various numbers of the holes 304 are arranged in various positions on the first foam material 302.

First foam layer 106 may be configured to allow for a first wound treatment therapy to be applied to first wound zone 102 (shown as a wound bed). For example, first foam layer 106 may be the coupling medium between a negative pressure pump and a fluid instillation pump configured to apply a cyclical application of negative pressure and fluid instillation to first wound zone 102 via first tube 116. In some embodiments, when negative pressure is applied to the first wound zone 102 via first foam layer 106, the first wound zone 102 may be caused to deform into the holes 304 by the negative pressure. Deformation of the first wound zone 102 into the multiple holes 304 may contribute to the breakdown of thick exudate, fibrinous slough, or other unwanted tissue or debris at the wound bed. The first foam material 302 and holes 304 may thereby facilitate debridement and/or cleansing of the wound bed to promote wound healing. Referring to FIG. 1A, first foam layer 106 may allow for the removal of air, fluid, wound exudate, etc. from the first wound zone 102 and the addition of instillation fluid to the first wound zone 102 via first tube 116. In other embodiments, first foam layer 106 may be provided without holes 304.

First Drape Layer

Figure 4:
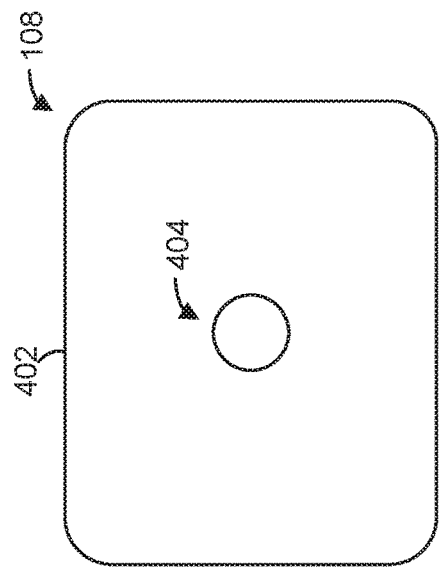
FIG. 4 is an illustration of a first drape layer used with the first wound zone separation system of FIG. 1A, according to an exemplary embodiment.

Referring now to FIG. 4, first drape layer 108 is shown, according to an exemplary embodiment. First drape layer 108 may be defined according to any number of, and combination of, desired dimensions, shapes, sizes, features, configurations, and other characteristics, and may be formed of any number of, or combination of, different materials. In the exemplary embodiment of FIG. 4, first drape layer 108 is shown to be defined by a first drape material 402 having a first drape hole 404 extending therethrough.

First drape hole 404 may be defined according to any number of desired dimensions, shapes, sizes, and configurations, and may be customized to fit a diameter defined by an exterior surface of first tube 116. In other embodiments, first drape layer 108 may provide any number of first drape holes 404. For example, first drape layer 108 may provide an additional number of first drape holes 404 to couple (e.g., fluidly, pneumatically, etc.) additional tubes with first foam layer 106. First drape hole 404 may include any number or combination of coupling features (e.g., flanged low-profile pads, fittings, snap-fit connectors, adhesive material, etc.) configured to couple first tube 116 about the first drape hole 404.

Referring to FIGS. 1A & 2A, first drape layer 108 is sealable over first wound zone 102 and at least a portion of second wound zone 104 in a substantially airtight manner to allow a pressure differential to be maintained across the first drape layer 108. For example, a negative pressure treatment may be applied to first wound zone 102 by establishing a pressure differential between a surface of first drape layer 108 nearest the first wound zone 102 and a surface of first drape layer 108 furthest the first wound zone 102. In some embodiments, first drape layer 108 is sealable over first wound zone 102 and at least a portion of second wound zone 104 in a substantially fluid-tight manner to prevent the transmission or migration of fluid from first wound zone 102 to second wound zone 104. For example, an instillation treatment may be applied to first wound zone 102 that is not intended to be applied to second wound zone 104. The placement of first drape layer 108 over first wound zone 102 and at least a portion of second wound zone 104 may prevent the transmission of instillation fluid to second wound zone 104. Additionally, the placement of first drape layer 108 over first wound zone 102 may be configured to prevent the transmission of wound exudate (e.g., wound fluid, wound exudate, etc.) between first wound zone 102 and second wound zone 104.

Second Foam Layer

Figure 5:
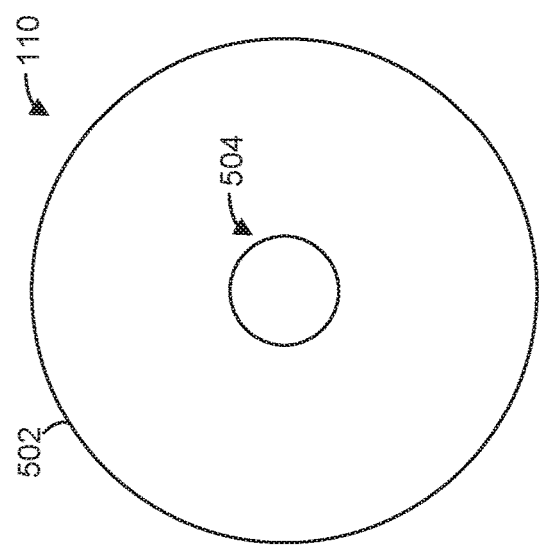
FIG. 5 is an illustration of a second foam layer used with the first wound zone separation system of FIG. 1A, according to an exemplary embodiment.

Referring now to FIG. 5, a top view of second foam layer 110 is shown, according to an exemplary embodiment. Second foam layer 110 may be defined according to any number of, and combination of, desired dimensions, shapes, sizes, features, configurations, and other characteristics, and may be formed of any number of, or combination of, different materials. In the exemplary embodiment of FIG. 5, second foam layer 110 is defined by a second foam material 502 (e.g., GRANUFOAM™ Dressing, V.A.C. VERAFLO CLEANSE CHOICE™ Dressing/Dressing Kit, etc.) having a second density and providing multiple holes 504 extending therethrough. In some embodiments, the second density of the second foam material 502 is less than the first density of the first foam material 302. Accordingly, the second foam material 502 may be formed of a material that is significantly different than a material that forms the first foam material 302. In some embodiments, the second foam material 502 is a felted foam material. In various embodiments, second foam layer 110 is shown to provide a central cutout 504 configured for placement about a circumference defined by first wound zone 102. In some embodiments, second foam material 502 may be the same or similar to first foam material 302.

The central cutout 504 is shown to be provided on second foam material 502 extending therethrough, according to an exemplary embodiment. Central cutout 504 may be defined according to any number of desired dimensions, shapes, sizes, and configurations appropriate for customization to first wound zone 102 and/or second wound zone 104. In some embodiments, central cutout 504 may be customized to fit a diameter defined by an exterior surface of first tube 116. In some embodiments, central cutout may be formed of equal or similar dimensions, shapes, and sizes to first drape hole 404. Referring to FIGS. 1A & 2A, central cutout 504 may be configured to align with first drape hole 404 such that a continuous, hollow aperture is formed therethrough. The continuous, hollow aperture formed by first drape hole 404 and central cutout 504 may allow for the transmission of first tube 116 through second foam layer 110 and first drape layer 108.

Second foam layer 110 may be configured to allow for a second wound treatment therapy to be applied to second wound zone 104. For example, second foam layer 110 may be the coupling medium between an instillation pump configured to apply an application of fluid instillation to second wound zone 104 via second tube 118. The dimensions, shapes, size, and configuration of second foam layer 110 and the material forming the second foam material 502 may be configured to allow for substantial saturation of fluid instillation.

Second Drape Layer

Figure 6:
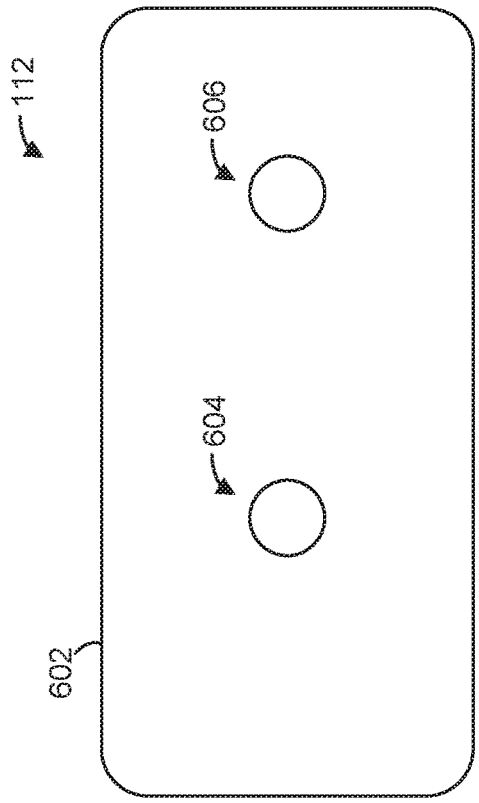
FIG. 6 is an illustration of a second drape layer used with the first wound zone separation system of FIG. 1A, according to an exemplary embodiment.

Referring now to FIG. 6, second drape layer 112 is shown, according to an exemplary embodiment. Second drape layer 112 may be defined according to any number of, and combination of, desired dimensions, shapes, sizes, features, configurations, and other characteristics, and may be formed of any number of, or combination of, different materials. In the exemplary embodiment of FIG. 6, second drape layer 112 is shown to be defined by a single material 602. Second drape layer 112 is shown to provide a second drape hole 604 and a third drape hole 606 extending therethrough.

Second drape hole 604 and third drape hole 606 may be defined according to any number of desired dimensions, shapes, sizes, and configurations. In some embodiments, second drape hole 604 and third drape hole 606 may define by equal or similar sizes and shapes. In some embodiments, second drape hole 604 may be customized to fit a diameter defined by first tube 116. In some embodiments, second drape hole 604 may be formed of equal or similar dimensions, shapes, and sizes to first drape hole 404 and/or first tube passage 506. Referring to FIGS. 1A & 2A, second drape hole 604 may be configured to align with first drape hole 404 and first tube passage 506 such that a continuous, hollow aperture is formed therethrough. The continuous, hollow aperture formed by second drape hole 604, first drape hole 404, and first tube passage 506 may allow for the transmission of first tube 116 through second drape layer 112, second foam layer 110, and first drape layer 108.

In some embodiments, third drape hole 606 may be customized to fit a diameter defined by second tube 118. In other embodiments, second drape layer 112 may provide any number of second drape holes 604 and/or third drape holes 606. For example, second drape layer 112 may provide an additional number of second drape holes 604 to couple (e.g., fluidly, pneumatically, etc.) additional tubes with first foam layer 106. Second drape hole 604 and third drape hole 606 may provide any number or combination of coupling features (e.g., flanged low-profile pads, fittings, snap-fit connectors, adhesive material, etc.) configured to couple first tube 116 with second drape hole 604 and second tube 118 with third drape hole 606.

Referring to FIGS. 1A & 2A, second drape layer 112 is sealable over second wound zone 104 in a substantially airtight manner to allow a pressure differential to be maintained across the second drape layer 112. For example, a negative pressure treatment may be applied to second wound zone 104 by establishing a pressure differential between a surface of second drape layer 112 nearest the second wound zone 104 and a surface of second drape layer 112 furthest the second wound zone 104. In some embodiments, second drape layer 112 is sealable over second wound zone 104 and in a substantially fluid-tight manner to prevent the transmission of fluid from second wound zone 104 to an external environment.

Manifold

Referring to FIG. 7, manifold 114 is shown, according to an exemplary embodiment. In some embodiments, manifold 114 may be configured to couple a common negative pressure pump (e.g., supplied by therapy device 128 or therapy device 126) with first wound zone 102 and second wound zone 104 to allow suction be drawn from both first wound zone 102 and second wound zone 104. As illustrated in FIG. 7, manifold 114 is shown to be defined by a rectangular plate formed of a single material 702. Manifold 114 is shown to provide a first manifold hole 704 and a second manifold hole 706 extending therethrough.

First manifold hole 704 and second manifold hole 706 may be defined according to any number of desired dimensions, shapes, sizes, and configurations. In some embodiments, first manifold hole 704 and second manifold hole 706 may define equal or similar sizes and shapes. First manifold hole 704 may be customized to fit a diameter defined by first tube 116. In some embodiments, first manifold hole 704 may be formed of equal or similar dimensions, shapes, and/or sizes to first drape hole 404, first tube passage 506, and/or second drape hole 604. In some embodiments, first manifold hole 704 may be configured to align with first drape hole 404, first tube passage 506, and second drape hole 604 such that a continuous, hollow aperture is formed therethrough. The continuous, hollow aperture formed by first manifold hole 704, second drape hole 604, first drape hole 404, and first tube passage 506 may allow for the transmission of first tube 116 through manifold 114, second drape layer 112, second foam layer 110, and first drape layer 108.

In some embodiments, second manifold hole 706 may be customized to fit a diameter defined by second tube 118. Referring to FIGS. 1A & 2A, second manifold hole 706 may be configured to align with third drape hole 606 such that a continuous, hollow aperture is formed therethrough. The continuous, hollow aperture formed by second manifold hole 706 and third drape hole 606 may allow for the transmission of second tube 118 through manifold 114 and second drape layer 112.

Fitting

Figure 8:
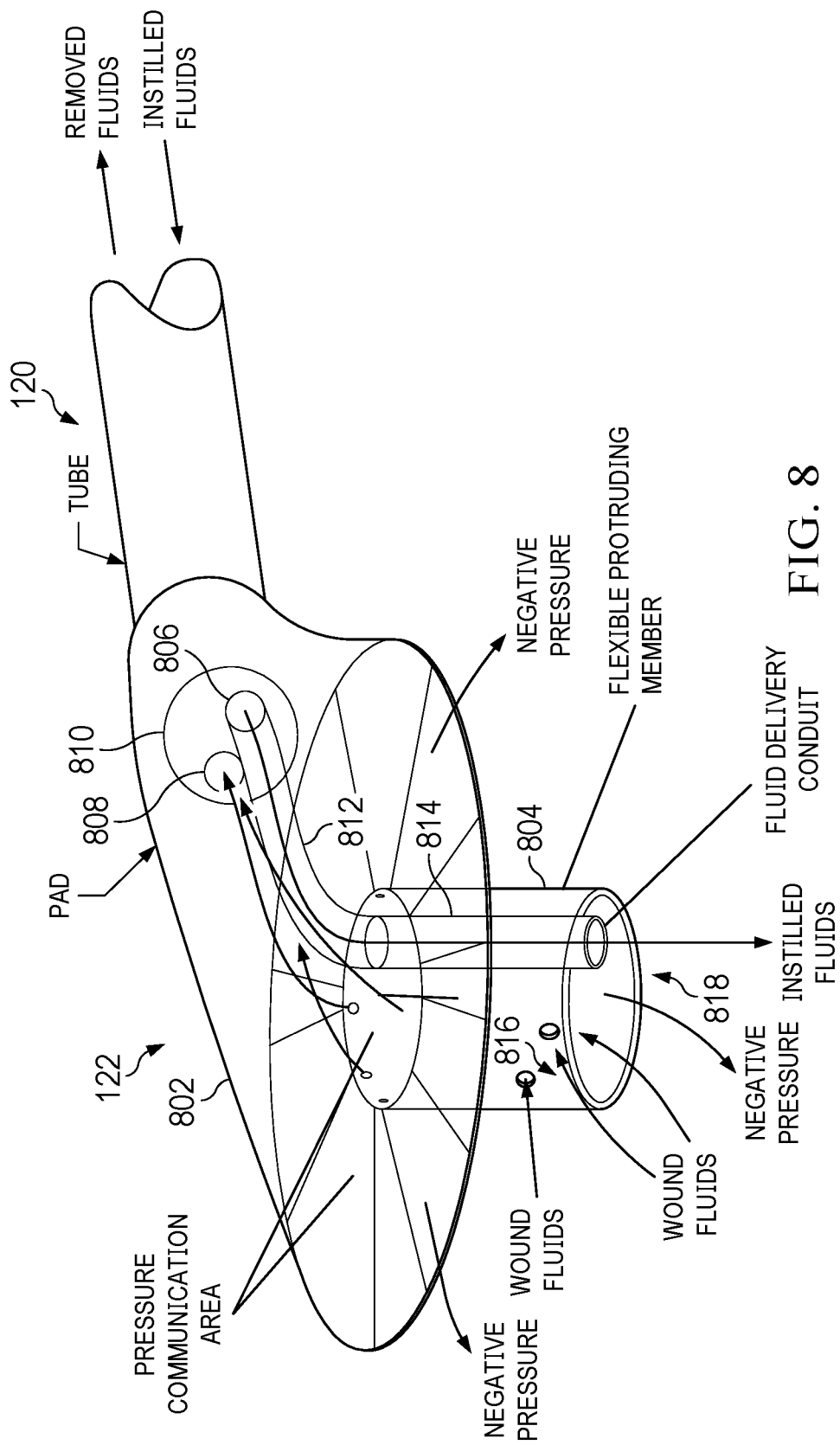
FIG. 8 is an illustration of a fitting used with the second wound zone separation system of FIG. 1B, according to an exemplary embodiment.

Referring now to FIG. 8, fitting 122 is shown, according to an exemplary embodiment. Fitting 122 is shown to include a top portion 802 and a bottom portion 804. Top portion 802 is shown to couple (e.g., physically, fluidly, etc.) tube 120 with bottom portion 804. Fitting 122 and tube 120 may be defined according to any number of, and combination of, desired dimensions, shapes, sizes, features, configurations, and other characteristics, and may be formed of any number of, or combination of, different materials.

In the embodiment of FIG. 8, tube 120 is configured to simultaneously apply an instillation therapy via a first passage 806 and a negative pressure therapy via a second passage 808. First passage 806 and second passage 808 may be defined as continuous hollow channels extending through an entirety of the length of tube 120. In the embodiment of FIG. 8, first passage 806 and second 808 are independent channels that are not fluidly coupled. First passage 806 may be configured to couple with an instillation pump (not shown). Additionally, second passage 808 may be configured to couple with a negative pressure source (not shown). In other embodiments, tube 120 may feature any number of channels configured to apply various wound treatment therapies.

In the embodiment of FIG. 8, top portion 802 and bottom portion 804 may be formed of the same material forming a unitary, monolithic structure. In other embodiments, top portion 802 and bottom portion 804 may be formed of the same or different materials and configured to couple (e.g., snap-fit, screw in, adhere in, etc.) to each other. For example, top portion 802 may provide a protruding threaded system while bottom portion 804 may feature an indented threaded structure in order to receive and install the protruding threaded system of top portion 802.

Top portion 802 is shown to include a tube aperture 810. Tube aperture 810 may be configured to receive tube 120 and couple (e.g., fluidly, pneumatically, etc.) tube 120 with the various components of fitting 122 and the features of wound zone separation system 100. In some embodiments, tube aperture 810 may include features (e.g., adhesive material, hook and loop structure, etc.) configured to retain the coupling of tube 120 with top portion 802. Top portion 802 is also shown to include a first instillation channel 812. First instillation channel 812 may be configured to direct an instillation treatment to an intended location in wound zone separation system 100 (e.g., first wound zone 102 via first foam layer 106). In the embodiment of FIG. 8, top portion 802 is shown to define a hollow volume configured to apply a negative pressure regimen. The hollow volume defined by top portion 802 may apply a negative pressure regimen via second passage 808.

Bottom portion 804 is shown include second instillation channel 814, according to an exemplary embodiment. Second instillation channel 814 may be defined as a continuous, hollow channel configured to extend through the entirety of bottom portion 804. In the embodiment of FIG. 8, second instillation channel 814 is shown to fluidly couple with first instillation channel 812 to form one continuous hollow channel extending through the entirety of fitting 122. When coupled with first instillation channel 812, an instillation therapy may be applied to first wound zone 102 via first passage 806.

Bottom portion 804 is shown include multiple holes 816, according to an exemplary embodiment. Holes 816 may be configured to fluidly couple the various components of wound zone separation system 100 with a negative pressure pump (not shown). In some embodiments, holes 816 may be configured to receive particles from first wound zone 102 and second wound zone 104. In various embodiments, various numbers of the holes 816 are arranged in various positions on the bottom portion 804.

Bottom portion 804 is shown to define an aperture 818, according to an exemplary embodiment. Aperture 818 may be configured to pneumatically couple and apply a negative pressure treatment to first wound zone 102. Additionally, aperture 818 may be configured to receive wound excrement (e.g., scar tissue, skin, fluid) from first wound zone 102.

Method of Applying Multiple Therapies

Referring to FIGS. 9A & 9B, various graphical representations of applying different wound therapies are shown, according to exemplary embodiments. The graphs illustrated in FIGS. 9A & 9B provide examples of simultaneously applying negative pressure therapies with instillation therapies.

Referring specifically to FIG. 9A, a first graphical representation of applying different wound therapies 900 is shown. A first graph 902 illustrates the cyclic application of negative pressure therapies while a second graph 904 illustrates the cyclic application of instillation therapy. The graph 902 shows pressure on the vertical axis 906 and time on the horizontal axis 908. The graph 904 shows instillation application on the vertical axis 910 and time on a similar horizontal axis 908.

Referring to FIG. 9B, a second graphical representation of applying different wound therapies 950 is shown, according to an exemplary embodiment. A third graph 952 illustrates a cyclic application of negative pressure 912 with an application of constant negative pressure 954. Second graph 904 is shown illustrating the application of instillation therapy 612. Similar to first graph 902, the third graph 952 shows pressure on the vertical axis 906 and time on the horizontal axis 908.

As illustrated by graph 902, a first application of negative pressure 912 is applied across first drape layer 108 of the first wound zone. A second application of negative pressure 914 is applied across second drape layer 112 of the second wound zone. As illustrated by graph 902, the negative pressure may cycle many times between a high value and a low value. In some embodiments, the low pressure value and the high pressure value may be user selectable. For example, the first application of negative pressure 912 may be varied between a value of approximately 25 mmHg and a value of approximately 200 mmHg and the second application of negative pressure may be varied between a value of approximately 10 mmHg and a value of approximately 150 mmHg. Other ranges may be used to suit pneumatic treatment therapies.

Alternatively, as illustrated by graph 952, a first application of negative pressure 912 may be applied across first drape layer 108 of the first wound zone. An application of substantially constant negative pressure 954 may be applied across second drape layer 112 of the second wound zone. As illustrated by graph 952, the application of constant negative pressure 954 may be maintained once the desired constant pressure value is achieved. Similar to the first application of negative pressure 912, the value of constant negative pressure may be user selectable.

In some embodiments, a control circuit within therapy device 126 and/or therapy device 128 may be used to control one or more negative pressure pumps to control the pressure of the various wound zones (e.g., first wound zone 102 and second wound zone 104) from atmospheric pressure to a target negative pressure as illustrated by graph 902. As illustrated by graph 902, the negative pressure may be maintained for a predetermined or user-selected amount of time once the target negative pressure has been achieved.

As illustrated by graph 904, a first application of fluid instillation 916 may be applied to first foam layer 106. First application of fluid instillation 916 may correspond to the low pressure values of graphs 902 and 952. For example, as illustrated by FIG. 9A, the application of fluid instillation 916 may occur after the first high-pressure application of negative pressure 912.

Although the graphs illustrated in FIGS. 9A & 9B show linear transitions (e.g., constant slopes) between pressure values and between instillation values, it should be understood that various other pressure trajectories may be provided by various embodiments. For example, the first application of negative pressure 912 may take a sinusoidal form in alternative embodiments of graph 902. Furthermore, while the example of graph 902 shows substantially equivalent rise times (e.g., the time for pressure to change from the low pressure value to the high pressure value) and fall times (e.g., the time for pressure to change from the high pressure value to the low pressure value), it should be understood that various relative rise times and fall times may be used. For example, a rise time and/or fall time may be selected by a user.

Figure 10A:
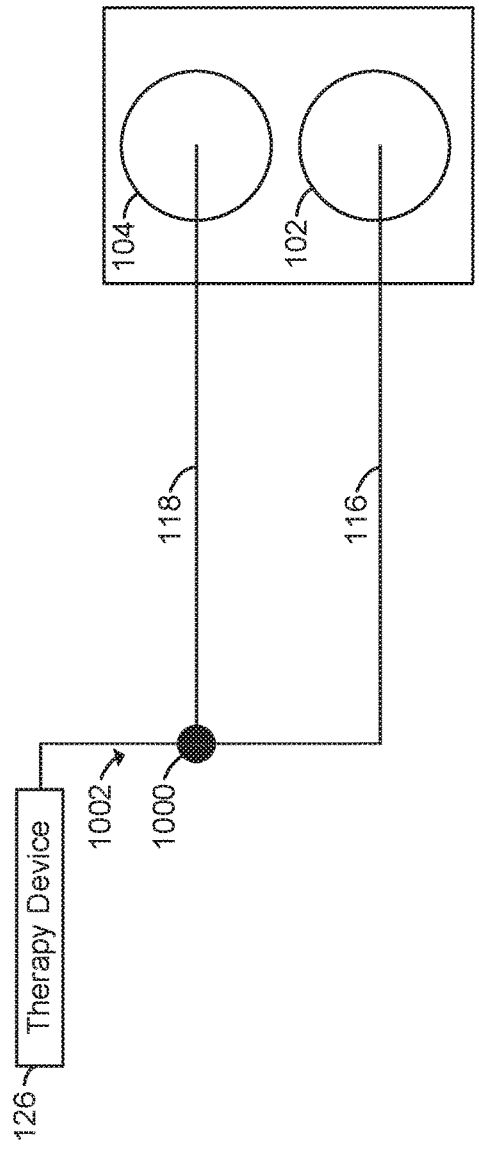
FIG. 10A is an illustration of a first tubing configuration used with the first wound zone separation system of FIG. 1A, according to an exemplary embodiment.

Referring generally to FIGS. 10A-10D, various embodiments of tubing configurations are shown schematically, according to exemplary embodiments. The examples provided in FIGS. 10A-10D are shown to be used with the wound zones of wound zone separation system 100. Referring specifically to FIG. 10A, a first configuration of tubing is shown to use first tube 116 with first wound zone 102 and second tube 118 with second wound zone 104.

In the embodiment of FIG. 10A, first tube 116 and second tube 118 are shown to couple at a connector 1000 for use with a common therapy device (e.g., therapy device 126). Connector 1000 may be any type of device configured to couple two tubes (e.g., first tube 116 and second tube 118) and lead into a singular tube 1002. Singular tube 1002 may be coupled (e.g., pneumatically, fluidly, etc.) to therapy device 126. In some embodiments, therapy device 126 may provide a negative pressure source and/or an instillation pump. In some embodiments, singular tube 1002 may be configured to transport instillation fluid from therapy device 126 to first tube 116 and/or second tube 118. In some embodiments, singular tube 1002 may be configured to transport wound exudate (e.g. wound debris, fluid, etc.) from first wound zone 102 and/or second wound zone 104 to a disposal bin (not shown).

Still referring to FIG. 10A, in the embodiments where singular tube 1002 is configured to transport instillation fluid from an instillation pump provided by therapy device 126, connector 1000 may be configured to direct flow in a predetermined direction. For example, connector 1000 may be configured to function as a check valve that only allows for instillation fluid to flow through first tube 116 into first wound zone 102. In some embodiments, connector 1000 may be configured to allow instillation fluid to flow through second tube 118. In other embodiments, connector 1000 may be configured to allow instillation fluid through both first tube 116 and second tube 118.

Figure 10B:
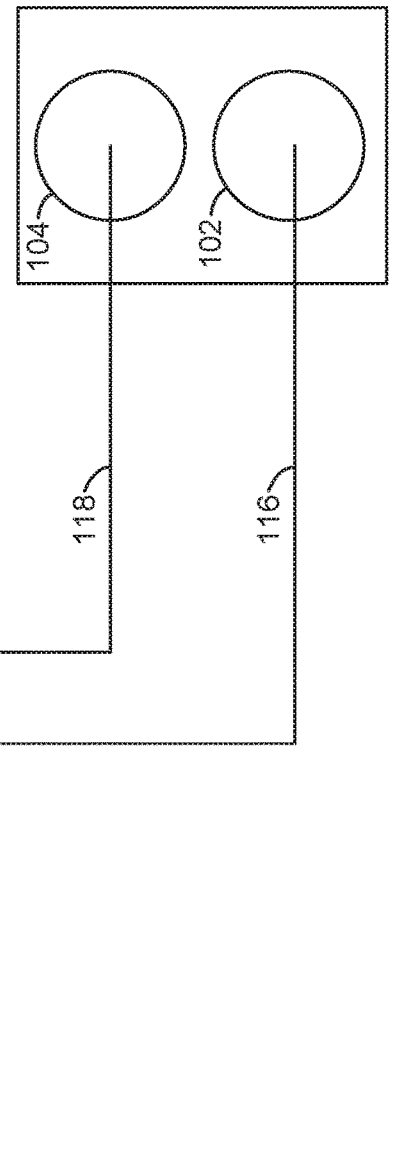
FIG. 10B is an illustration of a second tubing configuration used with the first wound zone separation system of FIG. 1A, according to an exemplary embodiment.

Referring now to FIG. 10B, a second configuration of tubing is shown for use with therapy device 126 and therapy device 128 (provided as separate devices), or a common therapy device (e.g., therapy device 126 or therapy device 128) with separate pump capabilities, according to an exemplary embodiment. The embodiment of FIG. 10B includes first tube 116 and second tube 118 function as independent tubes that are not connected (e.g., by connector 1000). In the embodiment of FIG. 10B, first tube 116 and second tube 118 may be coupled (e.g., fluidly, pneumatically) to separate negative pressure sources and/or different instillation pumps provided by therapy device 126 and therapy device 128.

Figure 10C:
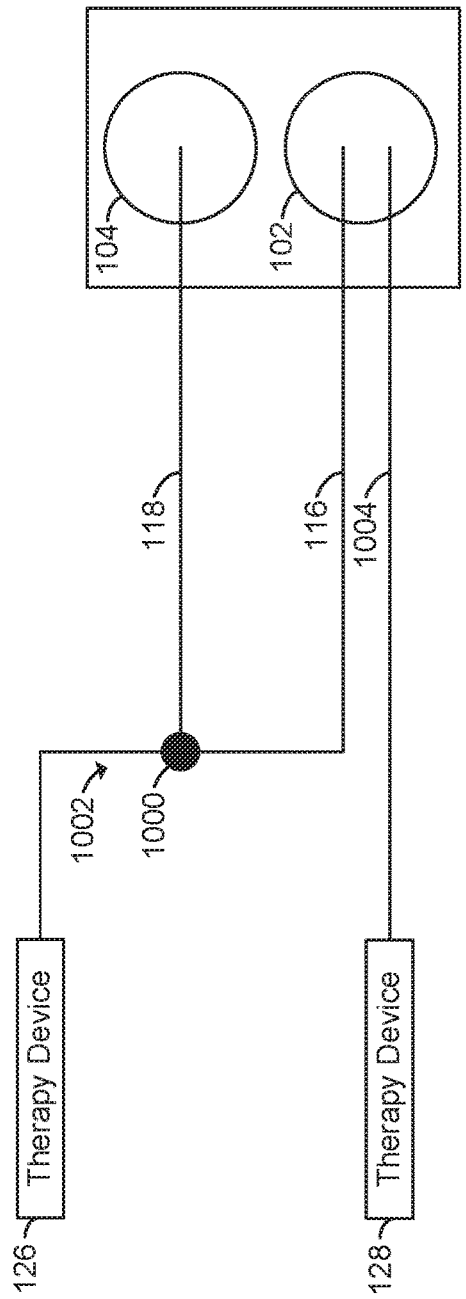
FIG. 10C is an illustration of a third tubing configuration used with the first wound zone separation system of FIG. 1A, according to an exemplary embodiment.

Referring now to FIG. 10C, a third configuration of tubing is shown, according to an exemplary embodiment. The embodiment illustrated in FIG. 10C shows first tube 116 and second tube 118 coupled using connector 1000 to singular tube 1002. In the embodiment of FIG. 10C, first wound zone 102 is also shown to be coupled (e.g., fluidly, pneumatically, etc.) with a third tube 1004. Third tube 1004 may be configured to apply a negative pressure provided by therapy device 128 to first wound zone 102 and/or transport instillation fluid to first wound zone 102.

Still referring to FIG. 10C, the tubing system formed by first tube 116, second tube 118, connector 1000, and singular tube 1002 may be coupled to a negative pressure pump provided by therapy device 126 and configured to apply a negative pressure therapy to first wound zone 102 and second wound zone 104. Third tube 1004 may be connected to an instillation pump provided by therapy device 128 and configured to apply an instillation therapy to first wound zone 102. In the embodiment of FIG. 10C, the application of a negative pressure therapy provided by therapy device 126 via the tubing system including first tube 116, second tube 118, connector 1000, and singular tube 1002 is separated from an instillation therapy provided by therapy device 128 applied by third tube 1004.

Figure 10D:
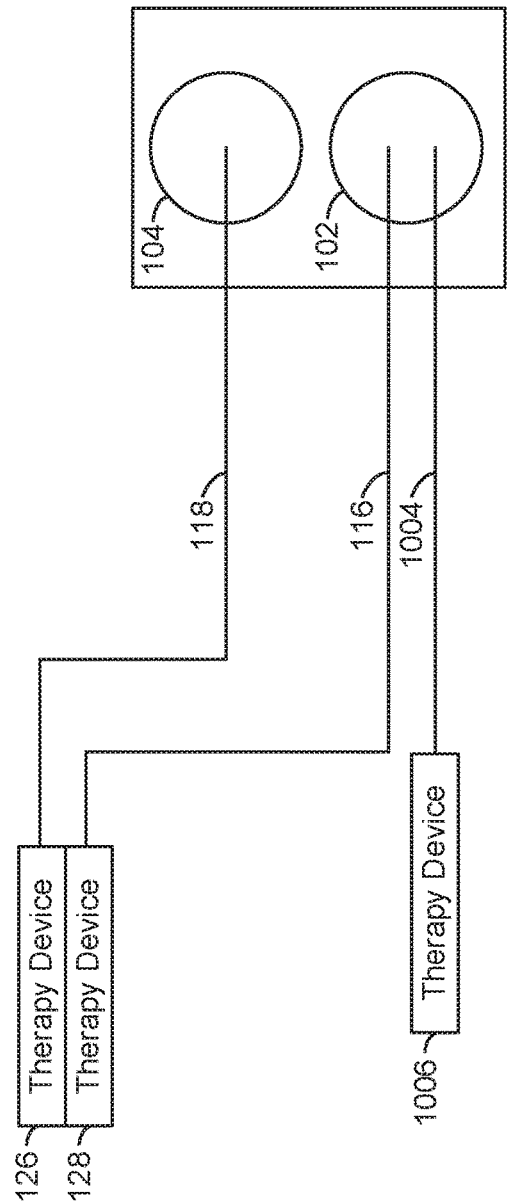
FIG. 10D is an illustration of a fourth tubing configuration used with the first wound zone separation system of FIG. 1A, according to an exemplary embodiment.

Referring now to FIG. 10D, a fourth configuration of tubing is shown, according to an exemplary embodiment. The embodiment illustrated in FIG. 10D includes therapy device 128 coupled to first wound zone 102 via first tube 116, therapy device 126 coupled to second wound zone 104 via second tube 118, and a therapy device 1006 coupled to first wound zone 102 via third tube 1004. The therapy device 1006 may provide substantially similar features and operational abilities as therapy device 126 and/or therapy device 128. In the embodiment of FIG. 10D, first tube 116 and second tube 118 may be coupled to different negative pressure sources provided by therapy device 126 and therapy device 128 and third tube 1004 may be coupled to instillation pump provided by therapy device 1006.

Configuration of Exemplary Embodiments

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

It should be noted that the terms "exemplary" and "example" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like, as used herein, mean the joining of two members directly or indirectly to one another. Such joining may be stationary (e.g., permanent, etc.) or moveable (e.g., removable, releasable, etc.). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," "between," etc.) are merely used to describe the orientation of various elements in the figures. It should be noted that the orientation of various elements may differ according to other exemplary embodiments, and that such variations are intended to be encompassed by the present disclosure.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

What is claimed is:

1. A system for use with at least two wound zones to apply at least two different wound therapies, comprising:
   a first foam layer configured for placement over a wound bed of a first wound zone;
   a second foam layer configured for placement over and in fluid communication with a periwound of a second wound zone, wherein at least a portion of the second foam layer and the second wound zone surround the first foam layer and the first wound zone;
   a first drape layer disposed over the first foam layer and at least partially beneath the second foam layer and configured to isolate the first wound zone from the second wound zone;
   a second drape layer disposed over the second foam layer and the first drape layer and configured to isolate the first wound zone and the second wound zone from an external environment;
   an instillation pump configured to provide an instillation fluid to the first foam layer;
   a negative pressure pump configured to remove air from the first wound zone and the second wound zone; and
   a control circuit communicably coupled to the instillation pump and the negative pressure pump.

2. The system of claim 1, wherein the control circuit is configured to control the instillation pump to:
   provide an amount of instillation fluid to the first foam layer;
   provide a soak period; and
   control the negative pressure pump to provide at least one cyclic variation of negative pressure at the first wound zone and the second wound zone.

3. The system of claim 1, further comprising a manifold configured to fluidly communicate the negative pressure pump with the first wound zone and the second wound zone.

4. The system of claim 3, wherein the manifold is configured to fluidly communicate the first foam layer with the instillation pump via a first tube.

5. The system of claim 3, wherein the manifold comprises a first aperture and second aperture and is configured to fluidly communicate the first foam layer and the second foam layer with the negative pressure pump via a first tube and a second tube.

6. The system of claim 3, wherein the manifold comprises a single aperture and is configured to fluidly communicate the first foam layer and the second foam layer with the negative pressure pump via a first tube.

7. The system of claim 3, wherein the manifold is configured to isolate a first cyclic variation of negative pressure applied to the first wound zone from a second cyclic variation of negative pressure applied to the second wound zone.

8. The system of claim 1, wherein the first drape layer comprises a first drape aperture configured to receive a first tube and the second drape layer comprises a second drape aperture configured to align with the first drape aperture of the first drape layer and receive the first tube and a third drape aperture configured to receive a second tube.

9. The system of claim 3, wherein the manifold comprises a first aperture and a second aperture configured to align with a second drape aperture and a third drape aperture.

10. The system of claim 1, wherein the control circuit is configured to simultaneously control the negative pressure pump to provide at least one cyclic variation of negative pressure at the first foam layer and the second foam layer and control the instillation pump to provide the instillation fluid to the first foam layer.

11. The system of claim 1, wherein the at least two different wound therapies comprise:
   a first wound therapy applied to the first wound zone comprising:
      a first application of negative pressure; and
      a first application of instillation; and
   a second wound therapy applied to the second wound zone comprising:
      a second application of negative pressure; and
      a second application of instillation.

* * * * *